United States Patent
Schaefer et al.

(10) Patent No.: US 9,358,088 B2
(45) Date of Patent: Jun. 7, 2016

(54) ORAL HYGIENE IMPLEMENT AND ORAL HYGIENE DEVICE

(71) Applicant: Braun GmbH, Kronberg (DE)

(72) Inventors: Norbert Schaefer, Frankfurt am Main (DE); Daniel Dietzel, Kelkheim (DE)

(73) Assignee: BRAUN GMBH, Kronberg (DE)

( * ) Notice: Subject to any disclaimer, the term of this patent is extended or adjusted under 35 U.S.C. 154(b) by 45 days.

(21) Appl. No.: 14/314,414

(22) Filed: Jun. 25, 2014

(65) Prior Publication Data
US 2015/0007398 A1     Jan. 8, 2015

(51) Int. Cl.
*A61C 17/22*     (2006.01)
*A61C 17/34*     (2006.01)
*A46B 5/00*     (2006.01)

(52) U.S. Cl.
CPC ........... *A61C 17/3436* (2013.01); *A46B 5/0095* (2013.01); *A61C 17/222* (2013.01)

(58) Field of Classification Search
CPC . A61C 17/3436; A61C 17/222; A46B 5/0095
See application file for complete search history.

(56) References Cited

U.S. PATENT DOCUMENTS

| | | |
|---|---|---|
| 2009/0007357 A1 | 1/2009 | Meadows et al. |
| 2012/0010049 A1 | 1/2012 | Amalaha |
| 2013/0060176 A1 | 3/2013 | Nicholas |

FOREIGN PATENT DOCUMENTS

| | | |
|---|---|---|
| EP | 2 550 938 A1 | 1/2013 |
| WO | WO 2013/014616 A1 | 1/2013 |

OTHER PUBLICATIONS

European Search Report for CM03858FQ dated Jan. 20, 2014.

*Primary Examiner* — Shay Karls
(74) *Attorney, Agent, or Firm* — Vladimir Vitenberg

(57) ABSTRACT

An oral hygiene implement attachable to a handle of an oral hygiene device is provided. The implement includes a housing; a functional element movably mounted at the housing such that it can be driven into a motion; a motion transmitter element coupled with the functional element; and an adhesive layer provided at the motion transmitter element for adhesively coupling the motion transmitter element with a drive shaft of the handle when being attached.

12 Claims, 5 Drawing Sheets

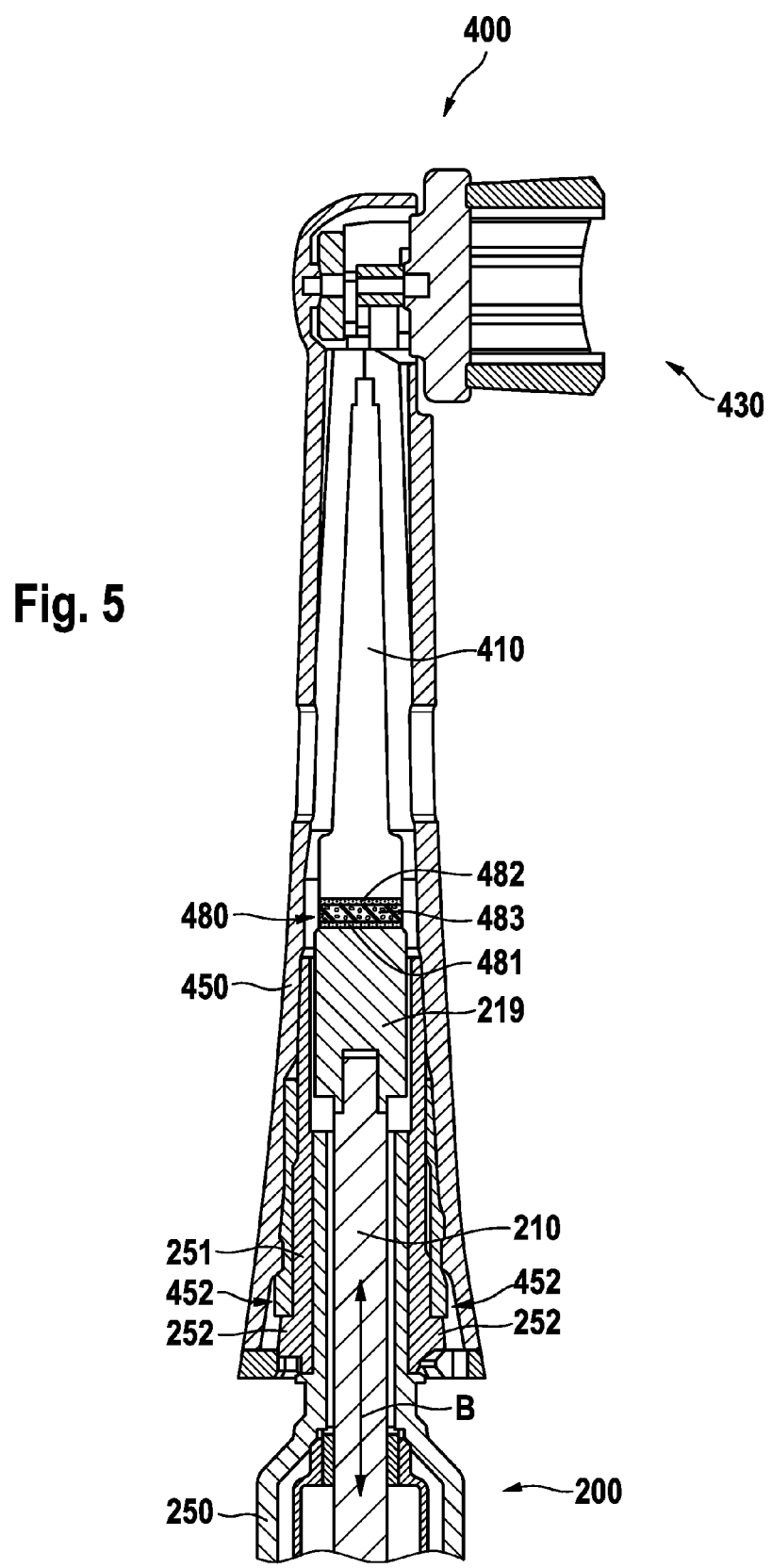

ORAL HYGIENE IMPLEMENT AND ORAL HYGIENE DEVICE

FIELD OF THE INVENTION

The present disclosure is directed to oral hygiene implements. More particularly, the present disclosure is directed to oral hygiene implements having a movably mounted functional element that is coupled with a motion transmitter element.

BACKGROUND OF THE INVENTION

It is known that for oral hygiene implements having a movably mounted functional element coupled with a motion transmitter element, the motion transmitter element may be functionally coupled with a drive shaft of a handle of an oral hygiene device by mechanical means (such as a snap-fit connection) or by magnetic means (e.g. a permanent magnet provided at the drive shaft couples with a magnetizable element provided at the motion transmitter element).

While the mechanical connection may suffer from tolerances between the coupling partners inevitably leading to noise and wear, a magnetic connection may suffer from much higher costs for being realized.

It is thus a desire of the present disclosure to provide an oral hygiene implement and oral hygiene device that overcome the mentioned shortcomings of the known coupling means.

SUMMARY OF THE INVENTION

In one embodiment, an oral hygiene implement attachable to a handle of an oral hygiene device is provided. The implement includes a housing; a functional element movably mounted at the housing such that it can be driven into a motion; a motion transmitter element coupled with the functional element; and an adhesive layer provided at the motion transmitter element for adhesively coupling the motion transmitter element with a drive shaft of the handle when being attached.

In another embodiment, an oral hygiene device is provided. The device includes a handle having a housing; and a drive shaft coupled to a drive. The device further includes an oral hygiene implement connected with the handle having a housing; a functional element movably mounted at the housing such that it can be driven into a motion; and a motion transmitter element coupled with the functional element. The device further includes an adhesive layer connecting the drive shaft with the motion transmitter element.

In another embodiment, a kit is provided. The kit includes at least one oral hygiene implement having a housing, a functional element movably mounted at the housing such that it can be driven into a motion, and a motion transmitter element coupled with the functional element; and an adhesive.

These and other features, aspects and advantages of specific embodiments will become evident to those skilled in the art from a reading of the present disclosure.

BRIEF DESCRIPTION OF THE DRAWINGS

The embodiments set forth in the drawings are illustrative in nature and not intended to limit the invention defined by the claims. The following detailed description of the illustrative embodiments can be understood when read in conjunction with the following drawings, where like structure is indicated with like reference numerals and in which:

FIG. 5 is a longitudinal cross-sectional cut to an upper portion of an oral hygiene device showing an oral hygiene implement being attached to a handle.

DETAILED DESCRIPTION OF THE INVENTION

Figure 1:
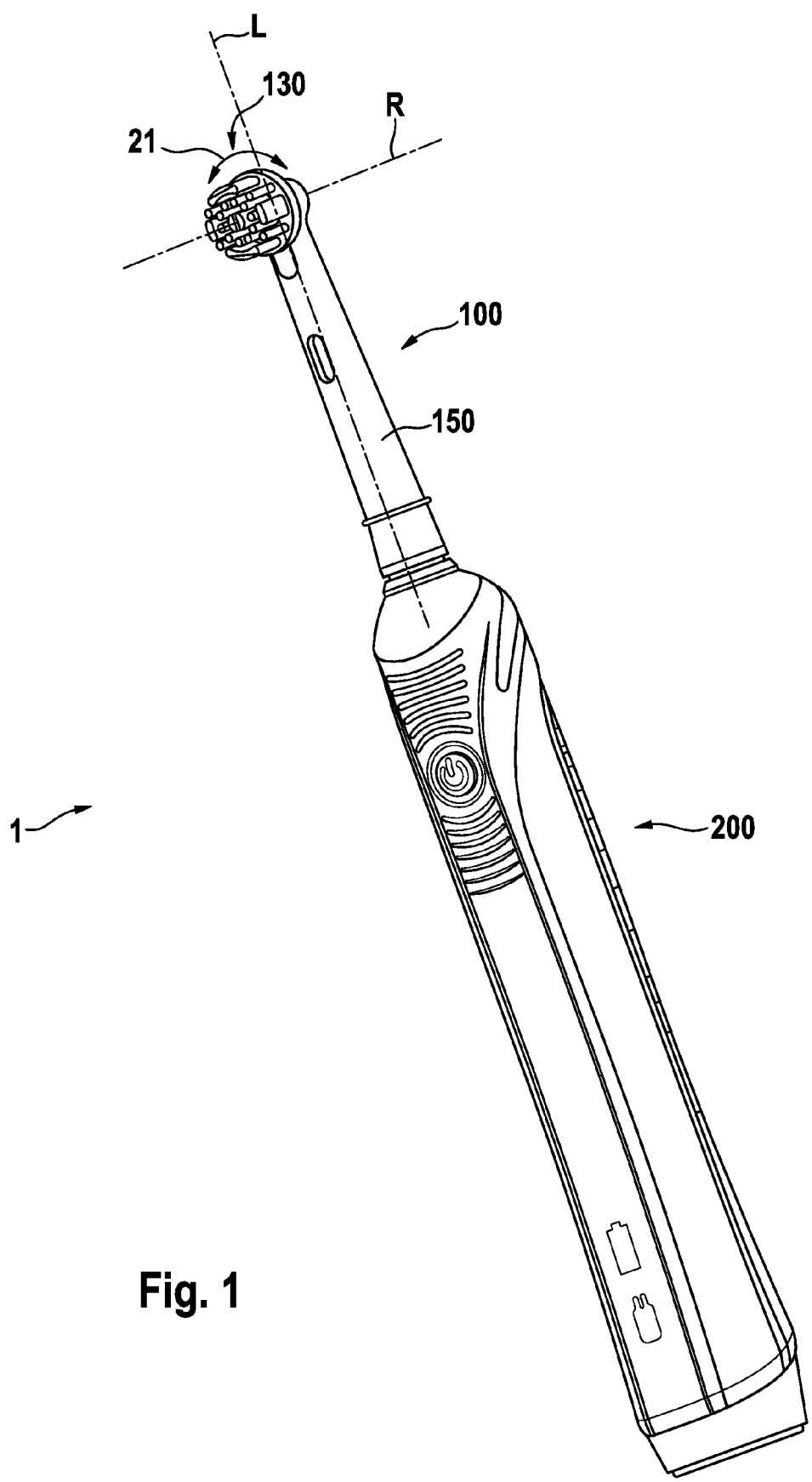
FIG. 1 is a depiction of an oral hygiene device according to embodiments shown and described herein.

The following text sets forth a broad description of numerous different embodiments of the present disclosure. The description is to be construed as exemplary only and does not describe every possible embodiment since describing every possible embodiment would be impractical, if not impossible. It will be understood that any feature, characteristic, component, composition, ingredient, product, step or methodology described herein can be deleted, combined with or substituted for, in whole or part, any other feature, characteristic, component, composition, ingredient, product, step or methodology described herein. Numerous alternative embodiments could be implemented, using either current technology or technology developed after the filing date of this patent, which would still fall within the scope of the claims. All publications and patents cited herein are incorporated herein by reference.

In some embodiments, the adhesive layer of the proposed oral hygiene implement or the oral hygiene device is realized as a glue layer, i.e. a single layer of more or less homogeneously disposed glue. Alternatively, the adhesive layer may be realized by an adhesive tape or strip, in particular a double sided adhesive tape or strip. Alternatively or additionally, the adhesive layer may have two or even more sub-layers, in particular the adhesive layer may have a core layer made in particular from a non-adhesive material (e.g. a foam), and two adhesive layers on the outer opposite surfaces of the core layer. In some embodiments, the core layer has a soft core layer (e.g. a soft foam) that is elastically compressible under pressure such that it elastically extends back into its original state when the pressure is released (i.e. a resilient core).

Instead of being realized at a motion transmitter element of an oral hygiene implement, the adhesive layer may be provided at a drive shaft of a handle of an oral hygiene device, where the drive shaft is intended to connect with a motion transmitter element of an oral hygiene implement. Alternatively, a kit may be provided comprising an oral hygiene implement as proposed, but without the adhesive layer, and an adhesive. The adhesive may be provided as packaged liquid or viscous glue or as a piece of an adhesive tape or strip.

The adhesive layer may comprise a protective foil that can be peeled away just prior to attaching the oral hygiene implement onto the handle in order to avoid that the adhesive material is drying/curing before the attachment process or to avoid that dust or other stuff adheres to the adhesive layer.

In some embodiments, the adhesive layer is chosen so that is provides a normal tensile strength of at least about 0.15 N/mm$^2$ and alternatively or additionally of not more than about 0.7 N/mm$^2$ Generally, all adhesive layers that provide a normal tensile strength between the motion transmitter element and the drive shaft of at least about 0.15 N/mm$^2$ and of not more than about 0.7 N/mm$^2$ are considered as in particular suitable for connecting a motion transmitter element of an oral hygiene implement and a drive shaft of a handle of an oral hygiene device.

"Normal tensile strength" of an adhesive bond in accordance with the present disclosure means the adhesive force required to separate two adhesively connected surfaces as defined by ASTM D897-08 "Standard Test Method for Tensile Properties of Adhesive Bonds".

One example of a double sided adhesive tape is 3M™ VHB™ Acrylic Foam Tape 4943F that is characterized by a normal tensile strength (T-block) of 58.5 N/cm² measured in accordance with ASTM D897-08 (after 72 hours of hardening time, to Aluminum at room temperature, 6.45 cm², jaw speed of 50 mm/minute). All normal tensile strength values in the present disclosure are to be understood as being measured under the same conditions.

Depending on the particular type of the oral hygiene device, a minimum absolute tensile strength (the absolute tensile strength being determined by the normal tensile strength of the adhesive layer and the area over which is will be effective) provided between the motion transmitter element and the drive shaft should be 3 N, 3.5 N, 4 N, 4.5 N, 5 N, 5.5 N, 6 N, 6.5 N, 7 N, 7.5 N, 8 N, 8.5 N, or 9 N. For an oral hygiene device realized as an electric toothbrush with the oral hygiene implement realized as a replacement brush head with a functional element realized as a cleaning element carrier mounted for oscillatory rotation, a minimum absolute tensile strength in the range of about 6.0 N to about 7.0 N has been found to be a sensible choice to avoid that the adhesive connection is too often separated as reconnection between the coupling partners may then not happen automatically and/or not with the same absolute tensile strength of the original (i.e. first) adhesive connection or the adhesive coupling may not be reestablished at all, e.g. because the adhesive layer has lost its stickiness. Thus, instead of realizing the minimum absolute tensile strength between the motion transmitter element and the drive shaft, an absolute tensile strength of above 6 N or 7 N could be realized. Further, it had been found that the maximum tensile strength should not be above 40 N, potentially not above 30 N, and further it may be chosen to be not above about 20 N as otherwise the manual separation in case of a worn-out replacement brush may not be simply achievable by a user or the user may fear to break the replacement brush. Thus, for the example oral hygiene device realized as an electric toothbrush with the oral hygiene implement realized as a replacement brush head with a functional element realized as a cleaning element carrier mounted for oscillatory rotation, the absolute tensile strength should be in the range of between about 6 N to about 40 N, in particular between about 6 N to about 30 N, and even more particular in between about 6 N and about 20 N. In particular, the upper limit of the tensile strength is chosen such that the adhesively connected parts can be essentially non-destructively separated (some adhesive may remain on each of the parts). In order to avoid repeated disconnection between the adhesive partners, the lower total tensile strength value may be chosen to be above about 6 N, in particular at least 7 N, 8 N, 9 N, 10 N, 11 N, 12 N, 13 N, 14 N, 15 N, 16 N, 17 N, 18 N, 19 N or about 20 N. Values between 10 N and 20 N may be preferred in order to avoid that the adhesive connection is unintentionally loosened or disconnected when an external force acts upon the functional element (e.g. keeps the functional element and thus the motion transmitter element in a locked position) while the drive of the oral hygiene device further tries to transfer a reciprocal linear motion via the motion transmitter element. The drive of the oral hygiene element may be realized such that it stops providing motion at an external force level already below the absolute tensile strength of the adhesive connection (e.g. the drive may stop at an external force of 10 N while the absolute tensile strength of the adhesive connection is 15 N).

In some embodiments, the surface of the motion transmitter element and the drive shaft used for adhesive connection may be in the range of between 19 mm² to 29 mm² (e.g. the connection surface may be circular with a diameter of between about 5 mm to about 6 mm). The absolute tensile strength of such a connection using a respective circular piece of the before mentioned doubled sided 3M™ VHB™ Acrylic Foam Tape 4943F would then be in the range of about 11.5 N to about 16.5 N (assuming that the above given normal tensile strength of 0.585 N/mm² would also be given between the motion transmitter element and the drive shaft).

The aspects of the present disclosure are further discussed by reference to figures showing particular example embodiments. Where a feature is not necessarily mandatory and thus should not necessarily be understood as a necessary disclosure of connected essential features, this is made clear by referring to such a feature by a "may be" clause.

FIG. 1 is a perspective depiction of an example embodiment of an oral hygiene device 1, here realized as an electric toothbrush. The oral hygiene device 1 comprises a handle 200 and an oral hygiene implement 100. Here, the oral hygiene implement 100 is realized as a replacement brush. The oral hygiene implement 100 has a functional element 130, here realized as a brush head, which functional element 130 is movably mounted at a housing 150 of the oral hygiene implement 100 such that the functional element 130 can be driven into a motion, e.g. an oscillatory rotation (as indicated with double arrow 21) around a rotation axis R that may be perpendicular to the longitudinal axis L of the oral hygiene implement 100. Instead of being realized as an electric toothbrush, the oral hygiene device may be realized as an (electric) tongue scraper, an (electric) flossing device, an (electric) interdental cleaner, a gum massaging device etc. The oral hygiene implement may then accordingly be realized as a tongue scraper section, a flossing section, an interdental cleaning section, a gum massaging section etc. The functional element may then accordingly be realized as a tongue scraper head, a flossing head, an interdental cleaning head, a massaging head etc.

Figure 2:
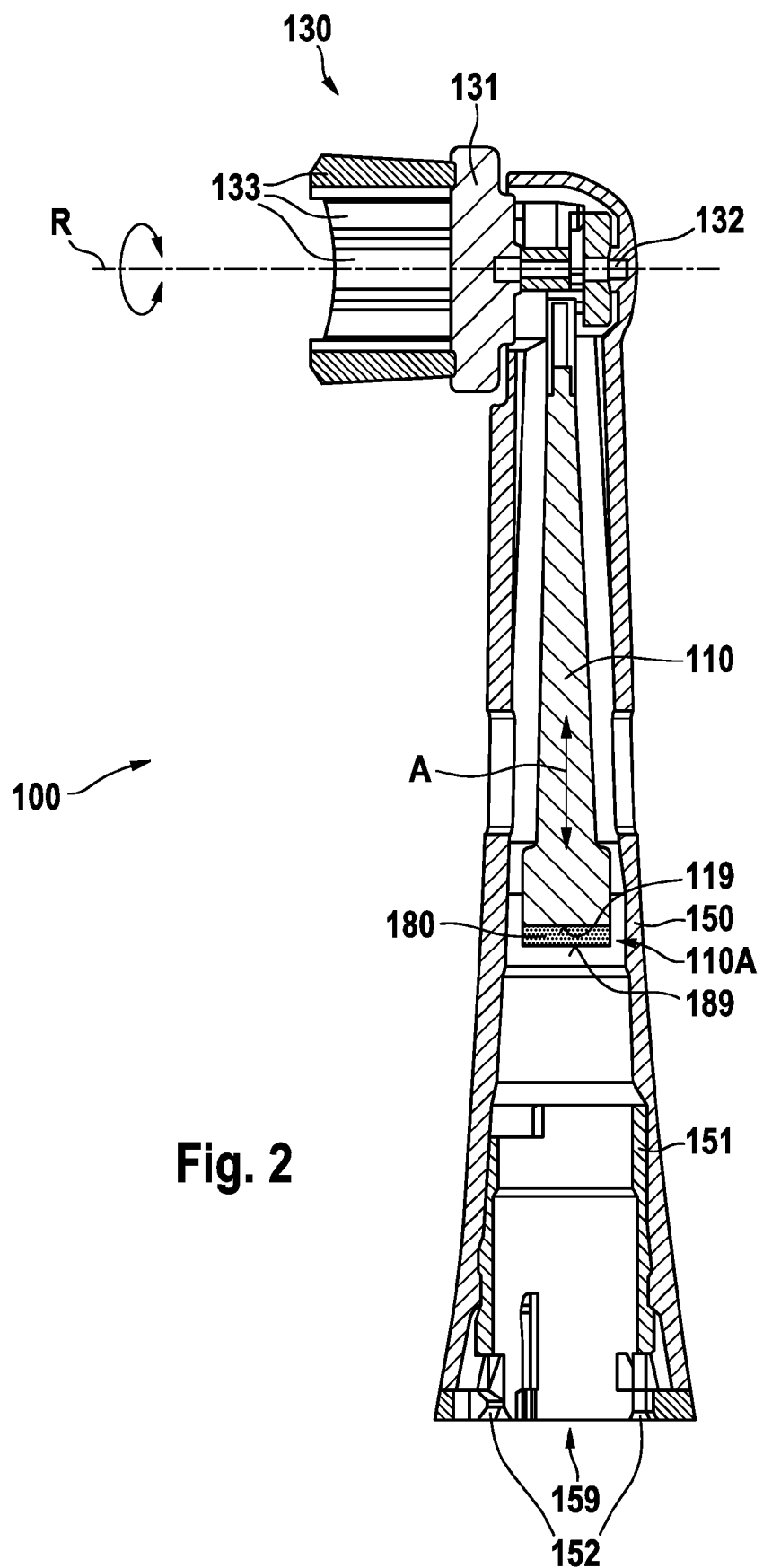
FIG. 2 is a longitudinal cross-sectional cut through an example oral hygiene implement.

FIG. 2 is a lateral cross sectional cut through an example embodiment of an oral hygiene implement 100 taken along a longitudinal axis of the oral hygiene implement 100. The oral hygiene implement 100 comprises a housing 150 and a functional element 130, which is movably supported at the housing 150.

The functional element 130 may comprise a carrier element 131 on which a plurality of cleaning elements 133 may be mounted for cleaning and massaging parts of the oral cavity such as teeth and gums. The carrier element 131 may be supported at the housing 150 by a mounting axle 132 for driven oscillatory rotation around a rotation axis R that in some embodiments is essentially perpendicular to the longitudinal axis (reference numeral L in FIG. 1) of the oral hygiene implement 100. In some embodiments, other movements are realized, e.g. an oscillatory rotation around a rotation axis essentially coinciding with or being essentially parallel to the longitudinal axis L.

The oral hygiene implement 100 further comprises a motion transmitter element 110 that in the shown embodiment is disposed within a cavity 159 formed within the implement housing 150. The motion transmitter element 110 is functionally connected with the functional element 130 as will be explained in more detail with reference to FIG. 3.

Generally and applicable to all embodiments, "functionally connected" shall mean a connection that is not intended to be disconnected and that shall enable that motion transmitted via the motion transmitter element is transferred to the functional element. The motion transmitter element 110 is arranged for transmission of a linear oscillatory movement to the functional element 130, which linear oscillatory motion may be generally parallel to the longitudinal axis of the oral hygiene implement 100 (as indicated by double arrow A). Such a linear oscillatory motion may be provided by a drive shaft of a handle when the oral hygiene implement 100 is in an attached state, as will be explained in more detail with reference to FIG. 5.

The motion transmitter element 110 has a first end 110A that is distal to the functional element 130. The motion transmitter element 110 has a coupling side 119 on its first end 110A that is oriented towards the opening provided at the distal end of the oral hygiene implement 100. The coupling side 119 may be flat and may essentially be lying in a plane perpendicular to the longitudinal axis. This shall not exclude that the coupling side may have any other form and may not be flat at all (and that it may in particular be a negative of the coupling side provided by the drive shaft of the handle to which the oral hygiene implement shall be attached). Generally and applicable to all embodiments, the coupling side 119 may be retracted from the opening at the end of the housing intended for coupling with a handle section so that the adhesive connection is established at a longitudinal position inside of the housing 150, in particular where this longitudinal location is retracted by a value lying in the range of between about 0.5 cm to about 5.0 cm, e.g. 1.0 cm, 1.5 cm, 2.0 cm, 2.5 cm, 3.0 cm, 3.5 cm, 4.0 cm, 4.5 cm or any other value lying in the mentioned range from the end of the attachment housing and the length of the housing 150 may be in the range of between about 3.0 cm to about 10.0 cm.

In some embodiments, as shown in FIG. 2, an adhesive layer 180 is provided on the coupling side 119 of the motion transmitter element. The adhesive layer 180 has a connection side 189 intended for getting into contact with a coupling side 219 of a drive shaft 210 of a handle 200 during an attachment procedure (see FIG. 4 for a depiction of an example embodiment of the handle) and for establishing an adhesive connection between the motion transmitter element 110 and the drive shaft. The adhesive layer 180 may have a protection foil (provided for being peeled away) on its coupling side 189 to avoid drying-out of the adhesive prior to the attachment process, i.e. the protection foil would be peeled away just shortly before the attachment process. Additionally or alternatively, the adhesive layer may be chosen such that the adhesive force with respect to the material of the motion transmitter element is higher than the adhesive force with respect to the material of the drive shaft to which adhesive coupling is intended. The adhesive layer may thus comprise two different adhesive components in a double-layer arrangement or the different materials of motion transmitter element and drive shaft may be chosen respectively. When being separated, the adhesive layer would stay on the motion transmitter element instead of remaining on the drive shaft. The coupling side 119 of the motion transmitter element 110 may at least partly be made from a plastic material or from a metal such as stainless steel.

While FIG. 2 shows the adhesive layer 180 already being provided on the first end 110A of the motion transmitter element 110, the oral hygiene implement and the adhesive may be provided to a consumer by means of a kit comprising at least one oral hygiene implement and at least one packaged adhesive, e.g. a tube with liquid or viscous glue such as an acrylate resin or at least one piece of double-sided adhesive tape or strip with its two adhesive sides being protected by a peelable protection foil. The adhesive tape or strip may already be provided in a pre-cut form. A consumer may then apply the adhesive onto the coupling side of the motion transmitter element of the oral hygiene implement and/or the coupling side of the drive shaft of the handle of the oral hygiene device in order to form the adhesive layer. In some embodiments, two different adhesives are provided, one for being applied onto the coupling side of the oral hygiene implement and one for being applied onto the coupling side of the drive shaft. The two different adhesives may be chosen as two components of a two-component adhesive.

The coupling side 119 provided at the first end of the motion transmitter element may have an area in the range of between about 1 mm$^2$ to about 100 mm$^2$, in particular in a range of between about 5 mm$^2$ to about 40 mm$^2$. The coupling side 119 may be circular and may have a diameter in the range of between about 1 mm and about 12 mm; in particular the diameter may be in a range of between about 4 mm and 8 mm. The area and shape of the coupling side 119 of the motion transmitter element may be chosen to coincide with the area and shape of the coupling side of the drive shaft to which the adhesive connection is intended.

The adhesive layer 180 may have a thickness in a range of between about 0.01 mm to about 5.0 mm, in particular of between about 0.1 mm and about 2.0 mm. The adhesive layer 180 may in particular have a soft core, which soft core may further in particular have resilient properties. A soft core of the adhesive layer 180 may efficiently reduce noise during operation of the oral hygiene device. The soft core can also balance linear motion provided by the shaft of an oral hygiene device even so an externally applied force (e.g. applied at the functional element) keeps the motion transmitter element in a locked position.

Figure 3:
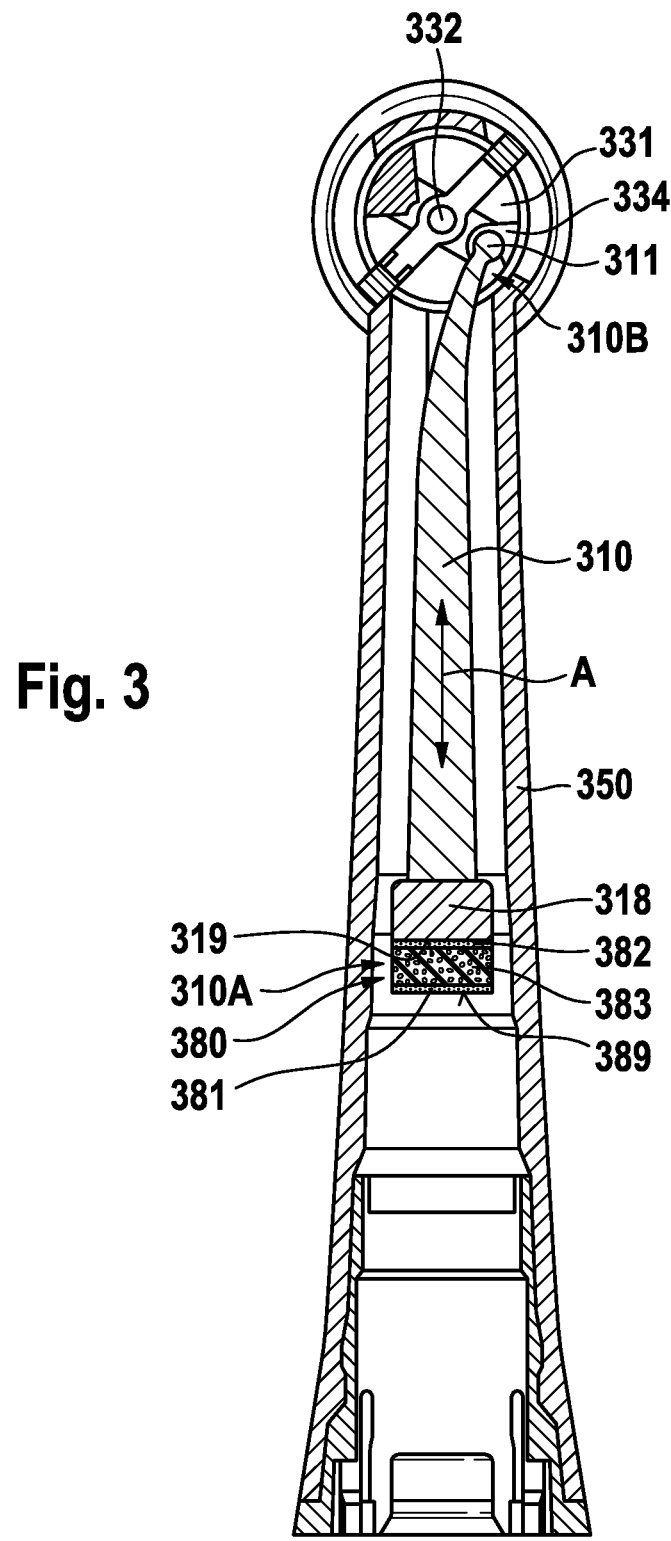
FIG. 3 is a longitudinal cross-sectional cut through another example oral hygiene implement taken at a 90 degrees pivoted cut-plane in comparison to FIG. 2.

The oral hygiene implement 100 as shown in FIG. 2 may further comprise an insert element 151 that is snapped into the attachment housing 150 thereby forming part of the housing 150. The insert element 151 may be equipped with a first coupling structure 152 intended for establishing a further coupling (i.e. a coupling different to the adhesive coupling) with a handle of an oral hygiene device in an attached state. In the shown example embodiment, the first coupling structure 152 is realized by mechanical coupling means such as snap hooks or spring elements for clamping projections provided at the handle section. In other example embodiments, the first coupling structure 152 may be realized by a magnetic coupling element. The longitudinal positions where the adhesive connection is established and where the further connection (e.g. mechanical connection) is established may be separated along the longitudinal direction, in particular by a distance lying in a range of between about 0.5 cm and about 5.0 cm. FIG. 3 is a transverse longitudinal cross-sectional cut through an example oral hygiene implement similar to the one shown in FIG. 2, where the viewing direction is towards the cleaning elements. As can be seen from FIG. 3, the motion transmitter element 310 is coupled to the functional element by a coupling pin 311 provided at a second end 310B of the motion transmitter element 310. The coupling pin 311 establishes a coupling with a coupling section 334 provided at the carrier element 331 at a position that is eccentric with respect to the rotation axis defined by the mounting axle 332. When the motion transmitter element 310 is driven into a linear oscillatory movement as indicated by double arrow A, then the carrier element 331 will be driven into an oscillatory rotation around its rotation axis. In some embodiments, the motion transmitter element 310 is associated with a return force element such as a biasing spring that biases the motion transmitter element into a defined rest position whenever the motion transmitter element is not being driven. In FIG. 3 it is shown, that a coupling element 318 may be provided at the first end 310A of the motion transmitter element 310, which coupling element 318 provides a coupling side 319. By such a coupling element 318, the coupling side 319 may be provided from a different material than the material of the motion transmitter element 310, which material may be chosen because of its suitability for establishing an adhesive coupling having a high tensile strength with the adhesive layer 380. While the motion transmitter element 310 may be made from metal such as brass, the coupling element 318 may be made from a different metal such as aluminum or stainless steel or the coupling element may be made from a plastic material.

The adhesive layer 380 is here realized as having three sub-layers 381, 382, and 383, where sub-layer 181 is the outer adhesive sub-layer providing a respective coupling side 389 for establishing an adhesive connection with a drive shaft of a handle of an oral hygiene device. The inner adhesive sub-layer 382 connects the adhesive layer 380 with the coupling element 318. A centre sub-layer 383 is here realized as a soft foam layer.

Figure 4:
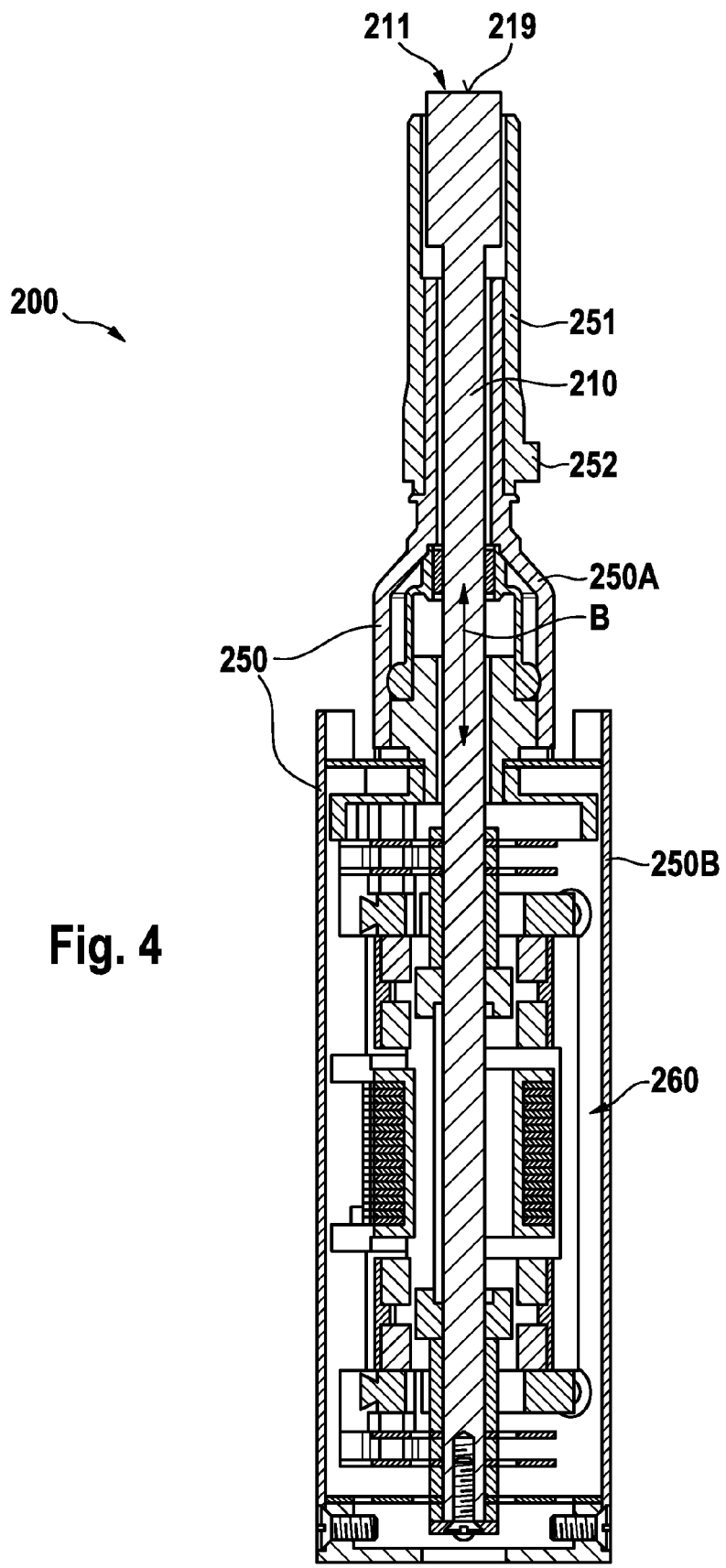
FIG. 4 is a longitudinal cross-sectional cut through a schematically shown handle of an oral hygiene device.

FIG. 4 shows a longitudinal cut through a schematic handle 200. In the shown example embodiment, the handle 200 comprises a drive shaft 210 that functions as a movable motor part of a resonant linear drive 260, which linear drive 260 is disposed within the handle housing 250. Obviously, the linear drive is just an example and any other motor (and gear arrangement) providing a linear oscillatory motion may be provided. During operation, the linear drive 260 provides for a linear oscillatory movement of the drive shaft 210 as is indicated by double arrow B. The drive shaft 210 has a coupling side 219 intended for getting into contact with the respective coupling side 189, 389 (shown in FIGS. 2 and 3) of the adhesive layer 180, 380 (shown in FIGS. 2 and 3) of the oral hygiene implement when being attached. Alternatively or additionally, an adhesive layer may be provided on the coupling side 219 of the drive shaft 210.

The handle section may comprise a handle housing at which a second coupling structure intended for establishing a connection with the first coupling structure provided at the oral hygiene implement is realized. In the shown example embodiment, the handle section 200 has a handle housing 250 comprising a top handle housing section 250A intended for coupling with the oral hygiene implement and a lower handle housing section 250B intended for being gripped by a user's hand. Here, the top handle housing 250A section comprises a top part 251 at which a second coupling structure 252 is realized. The second coupling structure 252 can form a further connection with the first coupling structure 152 (shown in FIG. 2) of the oral hygiene implement. FIG. 5 shows a longitudinal cross sectional cut of a oral hygiene implement 400 and a top housing section of a handle section 200 in an attached state. It is shown that the motion transmitter element 410 and the drive shaft 210 have established an adhesive connection via an adhesive layer 480 such that during operation, a linear reciprocation of the drive shaft 210 as indicated by double arrow B will be transferred to the functional element 430 via the motion transmitter element 410.

The adhesive layer 480 is here shown to comprise three sub-layers 481, 482, and 483 as had been explained in connection with FIG. 3. But of course the adhesive layer 480 may be realized as a single layer of an adhesive material as discussed with reference to FIG. 2.

Further, the first and second coupling structures 152 and 252 have established a further connection between the housing 150 of the oral hygiene implement and the handle housing 250 such that the oral hygiene implement 100 is fixed with respect to the handle housing 250.

In order to attach an oral hygiene implement as proposed with a handle of an oral hygiene device, the following steps may be performed:
1. Providing an oral hygiene implement as proposed either with a readily prepared adhesive layer (which may involve peeling away a protective foil provided over the adhesive layer) or applying an adhesive layer to a coupling side of a motion transmitter element, e.g. by gluing a double-sided adhesive tape onto the coupling side or by distributing a drop of liquid adhesive material onto the coupling side.
2. Providing a handle of an oral hygiene device suitable for attaching the oral hygiene implement onto it, which in particular implies that a shaft for providing a linear reciprocating motion is present, which shaft has a coupling side intended for being adhesively coupled with the adhesive layer provided at the coupling side of the motion transmitter element (where this step may additionally involve providing a shaft having a coupling side equipped with an adhesive layer or applying an adhesive layer onto the coupling side of the shaft—the adhesive layer may comprise an adhesive material representing one component of a two-component glue and the adhesive layer on the motion transmitter element may then comprise an adhesive material representing the second component of the two-component adhesive).
3. Moving the motion transmitter element into a position where it is in its most elongated state (i.e. where the coupling side is at a position most distal to the functional head of the oral hygiene implement) e.g. by manually moving the functional element to which the motion transmitter element is coupled into a position associated with this most distal position of the coupling side of the motion transmitter element.
4. Attaching the oral hygiene implement and the handle such that the coupling sides of the motion transmitter element and the shaft come into pressurized contact.
5. Holding this position for a period allowing the adhesive connection to establish.
6. Releasing the motion transmitter element from the elongated state.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The invention claimed is:

1. An oral hygiene implement having a longitudinal axis and attachable to a handle of an oral hygiene device, the implement comprising:
   a housing;
   a functional element movably mounted at the housing such that it can be driven into a motion;
   a motion transmitter element structured for reciprocal linear motion along the longitudinal axis and having a coupling side at its first end that is distal to the functional element, the motion transmitter element being coupled with the functional element; and
   an adhesive layer provided at the coupling side of the motion transmitter element for adhesively coupling the motion transmitter element with a drive shaft of the handle when being attached, for a reciprocal linear movement along the longitudinal axis.

2. The oral hygiene implement in accordance with claim 1, wherein the adhesive layer is realized by a glue layer.

3. The oral hygiene implement in accordance with claim 1, wherein the adhesive layer is realized by an adhesive tape or strip, in particular a double-sided adhesive tape or strip.

4. The oral hygiene implement in accordance with claim 1, wherein the adhesive layer has at least one soft core.

5. The oral hygiene implement in accordance with claim 1, wherein the adhesive layer has a normal tensile strength of at least about 0.15 N/mm$^2$.

6. The oral hygiene implement in accordance with claim 1, wherein the adhesive layer has a normal tensile strength of below about 0.7 N/mm$^2$.

7. The oral hygiene implement in accordance with any claim 1, wherein at least a part of the section of the motion transmitter element at which the adhesive layer is arranged is made from metal such as stainless steel or aluminum.

8. The oral hygiene implement in accordance with claim 1, wherein at least a part of the section of the motion transmitter element at which the adhesive layer is arranged is made from a plastic material.

9. An oral hygiene device having a longitudinal axis and comprising:
   a handle comprising
      a housing; and
      a drive shaft coupled to a drive;
   an oral hygiene implement connected with the handle comprising
      a housing;
      a functional element movably mounted at the housing such that it can be driven into a motion; and
      a motion transmitter element structured for reciprocal linear motion along the longitudinal axis and having a coupling side at its first end that is distal to the functional element, the motion transmitter element being coupled with the functional element; and
   a non-destructively separable adhesive layer provided at the coupling side of the motion transmitter element and connecting the drive shaft with the motion transmitter element for a reciprocal linear movement along the longitudinal axis.

10. The oral hygiene device in accordance with claim 9, wherein the adhesive layer has a higher adhesion force with respect to the motion transmitter element than with respect to the drive shaft.

11. A kit comprising:
   at least one oral hygiene implement having a longitudinal axis and comprising a housing, a functional element movably mounted at the housing such that it can be driven into a reciprocal linear motion along the longitudinal axis, and a motion transmitter element structurerd and configured to be coupled with the functional element; and
   an adhesive for coupling the functional element and the motion transmitter element for the reciprocal linear motion along the longitudinal axis.

12. The kit in accordance with claim 11, wherein the adhesive is selected from the group consisting of a packaged fluid, a viscous adhesive, at least one piece of an adhesive tape or strip and combinations thereof.

* * * * *